(12) United States Patent
Del Torto

(10) Patent No.: US 9,714,345 B2
(45) Date of Patent: Jul. 25, 2017

(54) SILICONE ELASTOMER MATERIAL SUITABLE FOR USE IN PARTICULAR FOR MAKING DENTAL IMPRESSIONS

(75) Inventor: Marco Del Torto, Milan (IT)

(73) Assignee: BLUESTAR SILICONES FRANCE SAS, Lyons (FR)

( * ) Notice: Subject to any disclaimer, the term of this patent is extended or adjusted under 35 U.S.C. 154(b) by 0 days.

(21) Appl. No.: 13/993,970

(22) PCT Filed: Dec. 12, 2011

(86) PCT No.: PCT/FR2011/000644
§ 371 (c)(1),
(2), (4) Date: Jun. 13, 2013

(87) PCT Pub. No.: WO2012/080594
PCT Pub. Date: Jun. 21, 2012

(65) Prior Publication Data
US 2013/0267628 A1    Oct. 10, 2013

(30) Foreign Application Priority Data
Dec. 13, 2010 (FR) ..................... 10 04844

(51) Int. Cl.
*A61K 6/10* (2006.01)
*A61C 9/00* (2006.01)
*C08L 83/06* (2006.01)
*C08L 83/04* (2006.01)
*C08G 77/12* (2006.01)
*C08G 77/20* (2006.01)

(52) U.S. Cl.
CPC .............. *C08L 83/06* (2013.01); *A61K 6/10* (2013.01); *C08L 83/04* (2013.01); *C08G 77/12* (2013.01); *C08G 77/20* (2013.01); *C08L 2203/02* (2013.01); *C08L 2205/025* (2013.01); *C08L 2205/03* (2013.01)

(58) Field of Classification Search
USPC .......................................... 523/109; 433/214
See application file for complete search history.

(56) References Cited

U.S. PATENT DOCUMENTS

| | | | |
|---|---|---|---|
| 2,526,043 A * | 10/1950 | Parr et al. | 106/38.35 |
| 2,825,811 A * | 3/1958 | Erickson et al. | 331/140 |
| 3,159,601 A | 12/1964 | Ashby | |
| 3,159,602 A | 12/1964 | Hamilton et al. | |
| 3,220,972 A | 11/1965 | Lamoreaux | |
| 3,377,432 A | 4/1968 | Abbott et al. | |
| 3,419,593 A | 12/1968 | Willing | |
| 3,445,420 A | 5/1969 | Kookootsedes et al. | |
| 3,715,334 A | 2/1973 | Karstedt | |
| 3,814,730 A | 6/1974 | Karstedt | |
| 3,989,667 A | 11/1976 | Lee et al. | |
| 4,450,283 A | 5/1984 | McAfee et al. | |
| 4,657,959 A | 4/1987 | Bryan et al. | |
| 4,699,813 A | 10/1987 | Cavezzan | |
| 4,741,966 A | 5/1988 | Cavezzan | |
| 5,047,444 A | 9/1991 | DeVoe et al. | |
| 5,118,559 A | 6/1992 | DeVoe et al. | |
| 5,182,316 A | 1/1993 | DeVoe et al. | |
| 5,403,885 A * | 4/1995 | Voigt et al. | 524/731 |
| 5,684,060 A * | 11/1997 | Konings et al. | 523/109 |
| 6,376,569 B1 | 4/2002 | Oxman et al. | |
| 6,998,427 B2 * | 2/2006 | Del Torto et al. | 523/109 |
| 2004/0236003 A1 | 11/2004 | Del Torto et al. | |
| 2006/0089427 A1 | 4/2006 | Yamamoto et al. | |
| 2008/0064790 A1 | 3/2008 | Canpont et al. | |

FOREIGN PATENT DOCUMENTS

| | | |
|---|---|---|
| DE | 198 01 657 A1 | 7/1999 |
| EP | 0 057 459 A1 | 8/1982 |
| EP | 0 188 978 A1 | 7/1986 |
| EP | 0 190 530 A1 | 8/1986 |
| WO | WO 93/17654 * | 9/1993 |
| WO | 98/58997 A1 | 12/1998 |
| WO | 00/00853 A2 | 1/2000 |
| WO | 02/102326 A1 | 12/2002 |

OTHER PUBLICATIONS

International Search Report issued on Apr. 11, 2012, by the European Patent Office as the International Searching Authority in corresponding International Patent Application No. PCT/FR2011/000644.

* cited by examiner

Primary Examiner — Tae H Yoon
(74) Attorney, Agent, or Firm — Dentons US LLP

(57) ABSTRACT

Described are organopolysiloxane compositions that are capable of cross-linking and/or of hardening by polyaddition reactions so as to produce elastomers or materials made of silicone. Further described, is how the composition is useful for making a dental impression in the context of preparing prostheses.

19 Claims, No Drawings

SILICONE ELASTOMER MATERIAL SUITABLE FOR USE IN PARTICULAR FOR MAKING DENTAL IMPRESSIONS

CROSS-REFERENCE TO PRIOR APPLICATIONS

This application is a National Stage of PCT/FR2011/000644, filed Dec. 12, 2011, and designating the United States (published in French on Jun. 21, 2012, as WO 2012/080594 A1), which claims priority under 35 U.S.C. §119 to FR 1004844, filed Dec. 13, 2010, each hereby expressly incorporated by reference in its entirety and each assigned to the assignee hereof.

The field of the present invention is that of organopolysiloxane compositions suitable for crosslinking and/or curing by polyaddition reactions to form elastomers or silicone materials which are useful especially for the taking of dental impressions as part of the production of prostheses. These elastomers or silicone materials are used to take an intraoral impression for a dental prosthesis such as a crown, an inlay, or a dental device.

The expression "taking impressions" in the present specification is understood to define not only the operations of taking impressions of an arbitrary object and arbitrary shape in order to produce a model, more particularly a plaster model, but also the operations of reproducing or duplicating models made more particularly of plaster. The expression "taking of dental impressions" in the present specification is intended to define not only the operations in which dental impressions are taken in the mouth in order to obtain exact reproductions of jaws or parts of jaws that do or not carry, entirely or partly, teeth, and to form plaster models, but also the operations of duplicating in which models of jaws or parts of jaws are reproduced in plaster in a dental prosthesis laboratory. The intended applications also encompass the manufacture of molded parts, other than duplicating compositions in dental applications.

In the dental field, the use of elastomers or silicone materials obtained by crosslinking and/or curing at room temperature, as a mold useful in the production of dentures, is continually growing. The precursor of this material is a composition having the consistency of a paste, into which a curing agent is introduced prior to use. The resulting mass then looses its pasty consistency to take on a "rubbery" and elastic consistency in the course of curing at the temperature of the patient's body. By virtue of its elasticity, it is then easy to remove the cured silicone elastomer from the mouth, and it can thereafter be used to cast a working model from it, in plaster, for example, from which the definitive denture is produced. The use of silicone elastomers is therefore widespread within the dental field. This is also due in part to the fact that the elastomers or silicone materials offer on the one hand a great diversity of chemical, mechanical, and physical characteristics and, on the other hand, a nontoxic, nonirritant, and nonallergenic character. Moreover, silicone materials constitute poor growth substrates for microorganisms, and this endows them with significant suitabilities with regard to hygiene.

Polyorganosiloxane compositions which crosslink by polyaddition are generally preferred within the dental impression sector since they allow elastomers or silicone materials to be obtained that are better quality from the standpoint both of mechanical properties and of precision of the shapes reproduced. These compositions are sold in two separate parts requiring mixing at the time of use, and are commonly referred to as two-component compositions. In compositions of this kind, formulated in two separate parts, one of the parts comprises at least polyorganosiloxane having per molecule at least two alkenyl groups each bonded to a silicon atom, and a catalyst, which is generally a compound of a metal from the platinum group, while the other part accommodates at least one polyorganosiloxane having per molecule at least two hydrogen atoms bonded to a silicon atom. The polymerization, crosslinking, or curing reaction of such compositions starts when the two parts are mixed—that is, the platinum-based catalyst, the polyorganosiloxane having per molecule at least two hydrogen atoms bonded to a silicon atom, and the polyorganosiloxane having per molecule at least two alkenyl groups. The crosslinking rate varies according to the amounts of catalyst. The reactivity of the composition can also be adjusted by adding agents which inhibit or retard the polyaddition reaction. These compounds are well known and act competitively with the catalyst, thereby retarding the crosslinking reaction.

After mixing of the two parts, the resulting composition begins to cure and the viscosity of the mixture increases; gelling ("gel setting") starts until there is irreversible transformation into a crosslinked polymer or "elastomer". When this gel setting point is reached, the composition flows with difficulty, and at a certain moment the composition can no longer be shaped by the user. Accordingly, a "working period" or "working time" is defined within which the composition remains able to be handled for an application such as the taking of a dental impression. When the reaction is finished (or virtually finished), the material or elastomer is said to have cured. This cure time is also an important parameter for a silicon impression material, since said material must remain in contact with the surface to be replicated until it has completely cured. Within the field of dental impressions, the working time required is often of the order of several minutes.

Accordingly, for applications which require the reproduction of details, such as the taking of a dental impression, the parameters of cure time and working time must be controlled carefully. However, one of the factors affecting both the working time and the cure time is the activity of the catalyst. It is known that catalysts based on platinum are sensitive to long storage periods (a year or more), and this may give rise to impairment of the crosslinking kinetics. This is manifested in an increase in the cure time. This cure time becomes increasingly long, and even unacceptable. The reason is that uncontrolled variation in the cure time jeopardizes the accuracy of an impression if the user withdraws the silicone material from the model to be copied before said material has completely polymerized. What is worse, blackening phenomena of the part comprising the platinum catalyst are also observed in the course of prolonged storage, making said part unusable.

Notably, this recurring problem has attracted a variety of approaches. For example, in U.S. Pat. Nos. 5,047,444, 5,118,559, and 5,182,316, the level of polymerization is controlled by detection of an ultraviolet fluorophore which is generated during the polymerization. This approach, however, necessitates the installation of additional apparatus such as a UV radiation source and a UV fluorescence detector.

Patent application DE-19801657-A1 describes the preparation of a derivative obtained by reacting a selection of compounds (such as starch, amylose, cellulose) with a platinum derivative in aqueous medium for 3 hours at preferably 60° C. Filtration and evaporation under reduced pressure gave a solid product with a yellow color and a Pt content of between 1% and 1.5% (see examples 1 and 2), which was identified as component (D). The starting products (for example, starch) were therefore removed by standard purification methods, and are therefore no longer present in the additive prepared. Furthermore, the compositions described are one-component compositions.

In a technical context of this kind, one of the essential objectives of the present invention is to overcome the problems encountered after long storage (1 year or more) of two-component polyaddition compositions catalyzed by a compound of a metal from the platinum group. The reason is that these compositions then exhibit retardation of the kinetics of the polyaddition reaction, and this is manifested in an increase in the working time and in a deterioration in the physical properties of the elastomer.

A second objective of the invention is to suppress the blackening phenomena observed after long storage (1 year or more) of the part comprising a catalyst, being a compound of a metal from the platinum group, of a two-component composition which crosslinks by polyaddition reactions.

In order to achieve this objective, among others, the inventors notably discovered, entirely surprisingly and unexpectedly, that the addition in sufficient amounts of a specific additive, called a stabilizer in the present specification, allows the problems set out above to be overcome.

Accordingly, the present invention, as its first subject, provides a composition X which is crosslinkable and/or curable by polyaddition reactions, taking the form of a two-component system S which comprises at least two separate parts A and B intended for mixing to form said composition X, and in which:

part A comprises:
(a) at least 25% by weight, relative to the total weight of part A, of at least one stabilizer D selected from the group of starches,
(b) at least one polyorganosiloxane V having per molecule at least two alkenyl, preferably vinyl, groups which are each bonded to a silicon atom,
(c) at least one catalyst C which is a compound of a metal from the platinum group, and part B comprises at least one polyorganosiloxane H having per molecule at least two hydrogen atoms which are bonded to an identical or different silicon atom.

The composition according to the invention has the advantage of being stable on storage even under extreme conditions of temperature and humidity. "Stable on storage" means that:
the kinetics of the polyaddition reaction catalyzed by the platinum is unaffected by long storage, and
the suppression of the phenomenon of blackening of the part containing the catalyst which is a compound of a metal from the platinum group.

Starch is a carbohydrate macromolecule which is present in many plants, especially in the reservoir organs such as the potato tuber, and in seeds (wheat, corn, rice, etc.), where it constitutes a form of glucose storage. In the starch molecule, glucose units connected by alpha 1-4 glycosidic bonds form helicoidal amylose chains, on which short chains of the same constitution branch off via alpha 1-6 glycosidic bonds. In starch, these branches are present approximately every thirty glucose residues. In the presence of iodine, starch takes on a blue-violet coloration.

The term "starch" also embraces so-called "modified" starches such as:
acid-treated starch;
base-treated starch;
bleached starch;
oxidized starch;
enzyme-treated starch;
monostarch phosphate;
glycerol starch;
distarch phosphate esterified with sodium trimetaphosphate;
phosphated distarch phosphate;
acetylated distarch phosphate;
starch acetate esterified with acetic anhydride;
starch acetate esterified with vinyl acetate;
acetylated distarch adipate;
acetylated distarch glycerol;
hydroxypropyl starch;
hydroxypropyl distarch phosphate;
hydroxypropyl distarch glycerol; and
sodium starch octenyl succinate.

According to one preferred embodiment, the stabilizer D is present at from 30% to 45% by weight, relative to the total weight of said part A.

With particular advantage, the stabilizer D is a corn starch.

The compound V is preferably a polyorganosiloxane having per molecule at least two alkenyl groups bonded to silicon, and which comprises:
(a) at least two siloxyl units of formula:

$$T_a Z_b SiO_{\frac{4-(a+b)}{2}} \quad (1.1)$$

in which:
the symbols T are identical or different $C_2$-$C_6$ alkenyl groups,
the symbols Z are identical or different monovalent hydrocarbon groups selected from the group consisting of an alkyl having 1 to 8 carbon atoms inclusive, optionally substituted by at least one halogen atom, advantageously, from the methyl, ethyl, propyl, and 3,3,3-trifluoropropyl groups and an aryl, advantageously, from the xylyl, tolyl, and phenyl radicals,
a is 1 or 2, b is 0, 1, or 2, and the sum a+b is 1, 2, or 3, and
(b) optionally at least one siloxyl unit of formula:

$$Z_c SiO_{\frac{4-c}{2}} \quad (1.2)$$

in which:
the symbol Z has the same meaning as above and c is 0, 1, 2, or 3.

The compound V is advantageously a polyorganosiloxane POS having a viscosity of between 10 and 200 000 mPa·s.

All of the viscosities referred to here correspond to a dynamic viscosity parameter which is measured, conventionally, at 25° C.

According to one particularly advantageous version, the composition X according to the invention comprises at least two polyorganosiloxanes V having per molecule at least two alkenyl groups each bonded to a silicon atom, preferably vinyl, and having dynamic viscosities x1 and x2 at 25° C. in the ranges 10 to 1000 mPa·s and from 1000 to 150 000 mPa·s respectively.

The polyorganosiloxane V may be solely formed of siloxyl units of formula (1.1) or may also contain siloxyl units of formula (1.2). It may also have a linear, branched, cyclic, or network structure.

Z is generally selected from methyl, ethyl, and phenyl radicals, and usually 60 mol % (or numerical percent) at least of the radicals Z are methyl radicals.

Examples of siloxyl units of formula (1.1) are the vinyldimethylsiloxyl unit, the vinylphenylmethylsiloxyl unit, the vinylmethylsiloxyl unit, and the vinylsiloxyl unit.

Examples of siloxyl units of formula (1.2) are $SiO_{4/2}$ siloxyl, dimethylsiloxyl, trimethylsiloxyl, methylphenylsiloxyl, diphenylsiloxyl, methylsiloxyl, and phenylsiloxyl units.

Examples of polyorganosiloxane V are linear and cyclic compounds such as the following: dimethylpolysiloxanes having dimethylvinylsilyl ends, (methylvinyl)-(dimethyl) polysiloxane copolymers having trimethylsilyl ends, (methylvinyl)-(dimethyl)polysiloxane copolymers having dimethylvinylsilyl ends; and cyclic methylvinyl-polysiloxanes.

The catalyst C, which is a compound of a metal from the platinum group, is well known to the skilled person. Use may more particularly be made of complexes of platinum with an organic product described in U.S. Pat. No. 3,159,601, U.S. Pat. No. 3,159,602, U.S. Pat. No. 3,220,972, and European patents EP-A-0 057 459, EP-A-0 188 978, and EP-A-0 190 530; and the platinum and vinyl organosiloxane complexes described in U.S. Pat. No. 3,419,593, U.S. Pat. No. 3,715,334, U.S. Pat. No. 3,377,432, and U.S. Pat. No. 3,814,730. The amount by weight of the catalyst C, calculated by weight of platinum metal, is generally between 2 and 400 ppm, and preferably between 5 and 200 ppm, based on the total weight of the polyorganosiloxanes V and H.

The polyorganosiloxane H is a polyorganosiloxane which has per molecule at least two hydrogen atoms bonded to the silicon, these Si—H groups being situated within the chain and/or at the chain end.

According to one preferred version, when the polyorganosiloxane V contains 2 alkenyl groups per molecule, the polyorganosiloxane H will be selected so as to contain at least 3 hydrogen atoms bonded to the silicon per molecule. Conversely, when the polyorgano-siloxane H contains 2 hydrogen atoms bonded to the silicon per molecule, the polyorganosiloxane V will be selected so as to contain at least 3 alkenyl groups per molecule.

The polyorganosiloxane H is more specifically a polyorganosiloxane comprising:
  (i) siloxyl units of formula:

$$H_d L_e SiO_{\frac{4-(d+e)}{2}} \quad (2.1)$$

in which:
  L is a monovalent hydrocarbon group which has no unfavorable effect on the activity of the catalyst and is preferably selected from alkyl groups having 1 to 8 carbon atoms inclusive, optionally substituted by at least one halogen atom; advantageously, from methyl, ethyl, propyl, and 3,3,3-trifluoropropyl groups, and also from aryl groups, and advantageously from xylyl, tolyl, and phenyl radicals,
  d is 1 or 2, e is 0, 1, or 2, and the sum "d+e" is 0, 1, 2, or 3,
  (ii) and optionally other siloxyl units, of average formula:

$$L_g SiO_{\frac{4-g}{2}} \quad (2.2)$$

in which:
  L has the same meaning as above and g is 0, 1, 2, or 3.

The dynamic viscosity of this polyorganosiloxane H is at least 10 mPa·s and is preferably between 20 and 1000 mPa·s.

The polyorganosiloxane H may be solely formed of siloxyl units of formula (2.1) or may additionally comprise siloxyl units of formula (2.2).

The polyorganosiloxane H may have a linear, branched, cyclic, or network structure.

The group L has the same meaning as the group Z described above.

Examples of siloxyl units of formula (2.1) are:

$$H(CH_3)_2SiO_{1/2}, HCH_3SiO_{2/2}, H(C_6H_5)SiO_{2/2}$$

The examples of units of formula (2.2) are the same as those given earlier on above for the units of formula (1.2).

Examples of polyorganosiloxane H are linear and cyclic compounds such as the following:
  dimethylpolysiloxanes having hydrogenodimethylsilyl ends,
  (dimethyl)(hydrogenomethyl)polysiloxane copolymers having trimethylsilyl ends,
  (dimethyl)(hydrogenomethyl)polysiloxane copolymers having hydrogenodimethylsilyl ends,
  hydrogenomethylpolysiloxanes having trimethylsilyl ends, and
  cyclic hydrogenomethylpolysiloxanes.

The ratio of the number of hydrogen atoms bonded to the silicon in the polyorganosiloxane H to the total number of groups with alkenyl unsaturation in the polyorganosiloxane V is between 0.4 and 10, preferably between 1 and 5.

According to one particular embodiment, part A and/or part B comprises at least one compound selected from the group consisting of the following: a reinforcing filler Q1, a bulking filler Q2, a retarder or inhibitor I of polyaddition reactions, a polyorganosiloxane gum G having per molecule at least two alkenyl, preferably vinyl, groups which are bonded to the silicon, and having a viscosity of greater than 1000 Pa·s at 25° C., a polydimethylsiloxane F used as diluent, a colorant K, a plasticizer P selected from the group consisting of liquid petroleum jelly and a paraffin, a wetting agent M, a silicone resin R, and a biocide N.

For the reinforcing filler Q1, the filler commonly used is a siliceous filler. Siliceous fillers suitable for use include all precipitated or pyrogenic silicas (or fumed silicas) known to the skilled person. It is of course also possible to use mixtures of different silicas. Preference is given to precipitated silicas and/or fumed silicas having a BET specific surface area of greater than 40 m²/g, and more specifically between 50 and 300 m²/g. More preferably, fumed silicas are used that have the aforementioned specific surface area characteristics. More preferably still, fumed silicas are used that have a BET specific surface area of between 100 and 300 m²/g. Generally speaking, this reinforcing filler has an average particle size of less than 0.1 µm.

These silicas can be incorporated as they are or following treatment with organosilicon compounds commonly used for that purpose. Such compounds include methylpolysiloxanes such as hexamethyldisiloxane, octamethyldisiloxane, octamethylcyclotetrasiloxane, methylpolysilazanes such as hexamethyldisilazane and hexamethylcyclotrisilazane, chlorosilanes such as dimethylchlorosilane, trimethylchlorosilane, methylvinyldichlorosilane, and dimethylvinylchlorosilane, and alkoxysilanes such as dimethyldimethoxysilane, dimethylvinylethoxysilane, and trimethylmethoxysilane. During such treatment the silicas may increase their initial weight to a level of 20%, preferably 18% approximately. It is noteworthy that the particulate siliceous mineral filler may advantageously be employed in the form of the suspension obtained by treating the filler by application of the method in accordance with the teaching of patent applications WO-A-98/58997 and WO-A-00/00853, which envisage two-stage treatment of the filler with a compatibilizer (selected for example from: for the first treatment stage, a silazane, a hydroxy siloxane, an amine, or an organic acid; and, for the second treatment stage, a silazane) and operating in the presence of the POS constituent (1). Where such treatment leads to a basic pH, it is possible to add a neutralizing agent such as a weak acid, for example, to the dispersion. Such particular treatment of the filler is advantageous when it is necessary to retain excellent fluidity for the silicone material (in the noncrosslinked state). These fillers, when present, are added at from 2% to 30%, preferably even 3% to 20%, relative to the total weight of the composition.

The bulking filler Q2 generally has a particle diameter of greater than 0.1 µm, and is selected preferably from ground quartz, zirconias, calcined clays, diatomaceous earths, optionally surface-treated calcium carbonate, aluminum silicates and/or sodium silicates, aluminas, titanium oxide, and mixtures of these species. On a weight basis, the bulking fillers Q2, when used, are present in the silicone material at from 5% to 60% by weight, relative to the total weight of the composition X.

The agents I which inhibit polyaddition reactions are well-known compounds. Use may be made in particular of organic amines, organic oximes, diesters of dicarboxylic acids, acetylenic alcohols, acetylenic ketones such as ethynylcyclohexanol, and vinylmethyl-cyclopolysiloxanes (see, for example, U.S. Pat. No. 3,445,420 and U.S. Pat. No. 3,989,667). When present in the composition, the inhibitor is used at from 0.005% to 5% by weight, preferably from 0.01 to 3 parts by weight per 100 parts by weight of the polyorganosiloxane V.

The dynamic viscosity of polydimethylsiloxane F which is used as a diluent, at 25° C., is generally between 10 and 5000 mPa·s and preferably between 20 and 1000 mPa·s.

According to one preferred embodiment, the wetting agent M is a surfactant. Examples of wetting agent M include those from international application WO-A-2002102326, more particularly the following compounds:

an ester obtained by esterifying a $C_{13}$ fatty acid (lauric acid) with a poly(oxyethylene) glycol containing approximately 9 oxyethylene units, having an HLB of 13.1, sold under the name Lincol PE 400 ML;

a polyethoxylated $C_{13}$ saturated aliphatic alcohol containing approximately 8 oxyethylene (OE) units, having an HLB of 12.8, sold under the name Rhodasurf ROX;

a polyalkoxylated $C_8$ saturated aliphatic alcohol containing a number of oxyethylene and oxypropylene (OP) units such that the molecular mass Mw of the polyalkoxylated alcohol is approximately 1000 g/mol, sold under the name Tegopren LP 111 (abbreviated to TA3);

a polyalkoxylated $C_{10}$-$C_{12}$ saturated aliphatic alcohol containing approximately 4 oxyethylene units and 3 oxypropylene units, having an HLB of 7, sold under the name Antarox FM 33 (abbreviated to TA4);

a polyethoxylated $C_{12}$ saturated aliphatic alcohol containing approximately 2 oxyethylene units, having an HLB of 8.1, sold under the name Rhodasurf OT/2.

Other wetting agents M include nonionic, ionic, or amphoteric surfactants. The agents used will be selected as required in a form in which they are compatible for contact with the skin and the mucosae, especially the buccal mucosae: they must be nontoxic, nonallergenic and nonirritant at the doses used.

The nonionic surfactants include in particular the following: polyalkoxylated fatty acids; polyalkoxylated alkylphenols; polyalkoxylated fatty alcohols, polyalkoxylated or polyglycerylated fatty amides; polyalkoxylated fatty amines; polymers resulting from the condensation of ethylene oxide and/or propylene oxide with ethylene glycol and/or propylene glycol; polymers resulting from the condensation of ethylene oxide and/or propylene oxide with ethylenediamine; polyalkoxylated terpenic hydrocarbons; polydiorganosiloxanes containing siloxyl units which carry ethylene oxide chain sequences and/or propylene oxide chain sequences; polydiorganosiloxanes containing siloxyl units which carry polyol-type chain sequences; polyalkoxylated silanes or polysilanes; alkylglucosides, alkylpolyglucosides; sugar ethers; sugar esters; sugar glycerides; sorbitan esters; ethoxylated compounds of these sugar derivatives; and mixtures of these surfactants.

The anionic surfactants include in particular: alkylbenzenesulfonates, alkyl sulfates, alkyl ether sulfates, alkylaryl ether sulfates, alkyl succinates, alkyl carboxylates, alkyl derivatives of protein hydrolysates, alkyl and/or alkyl ether and/or alkylaryl ether phosphate esters in which the cation is generally an alkali metal or alkaline-earth metal; and mixtures of the aforementioned surfactants.

The cationic surfactants include in particular: trialkylbenzylammonium halides; tetraalkylammonium halides; and mixtures of these surfactants.

The amphoteric surfactants include in particular: alkylbetaines, alkyldimethylbetaines, alkylamidopropylbetaines, alkylamidopropyldimethylbetaines, alkyltrimethylsulfobetaines; imidazoline derivatives such as alkylamphoacetates, alkylamphodiacetates, alkylamphopropionates, alkylamphodipropionates; alkylsultaines, alkylamidopropylhydroxysultaines; condensation products of fatty acids and protein hydrolysates; amphoteric derivatives of alkylpolyamines; proteins and protein hydrolysates; and mixtures of these surfactants.

Specific examples of nonionic surfactants are as follows:

(a) polyalkoxylated $C_8$-$C_{22}$ aliphatic alcohols containing from 2 to 25 alkoxy units, as for example oxyethylene (OE) and/or oxypropylene (OP) units;

(b) polydiorganosiloxanes containing siloxyl units which carry ethylene oxide chain sequences and/or propylene oxide chain sequences; examples include the surfactants of formulae I, II, and III that are described in patent U.S. Pat. No. 4,657,959; and (c) mixtures of surfactants (a) with one another, mixtures of surfactants (b) with one another, and mixtures of one or more surfactants (a) with one or more surfactants (b).

The surfactant or surfactants is or are added in an amount of not more than 10% and preferably not more than 5%, relative to the total weight of the composition X.

For the colorant K, organic and/or inorganic color pigments known in the field may be used.

With regard to the biocide N which may be employed in the composition according to the invention, it should be noted that this biocide is preferably selected from the group of active-chlorine precursors based on N-chlorinated compounds comprising:

chloramine B (sodium N-chlorobenzenesulfonamide),
chloroamine T (sodium N-chloro-p-toluenesulfonamide),
dichloroamine T (N,N-dichloro-p-toluenesulfonamide),
N-trichloromethylmercapto-4-cyclohexene-1,2-dicarboxylamide,
halazone (benzoic acid p-n-dichlorosulfonamide),
N-chlorosuccinimide,
trichloromelamine,
chloroazodine

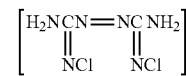

N-chloro derivatives of cyanuric acids, preferably trichloroisocyanuric acid and/or sodium dichloroisocyanuric dihydrate,
N-chlorohydantoins, preferably 1-bromo-3-chloro-5,5'-dimethylhydantoin, or 1,3-dichloro-5,5'-dimethylhydantoin,
and mixtures thereof.

This group of antiseptics correspond substantially to the class of N-chloroamines, which comprises the derivatives of amines in which one or two of the valences of the trivalent nitrogen are substituted by chlorine. In the presence of water, the N-chloroamines produce hypochlorous acid HClO or salts of this acid such as NaClO. HClO and NaClO are active chlorine derivatives which are endowed with a high bactericidal capacity, which can be exploited in the context of the invention (this is case especially when said material is intended for the taking of dental impressions in the mouth). At least one different antiseptic auxiliary may advantageously be associated with antiseptics which operate by release of chlorine and which are preferably selected from the group of formulations comprising one or more quaternary ammoniums (for example, benzalkonium chloride), and optionally at least one sequestrating activator, preferably selected from complexing agents for metal ions (for example, EDTA or ethylenediaminetetraacetic acid).

The concentration of biocide(s), when used, is not more than 1%, preferably not more than 0.8%, and more preferably still between 0.001% and 0.5% by weight, relative to the total mass of the composition according to the invention.

According to one particular embodiment, a composition X according to the invention is obtained by mixing the parts A and B in ratios by weight of between 1:10 to 1:1 respectively and preferably by mixing, by weight, 1 part of A and 5 parts of B.

According to another particular embodiment the composition X according to the invention is characterized in that:
(1) part (A) comprises:
  at least two polyorganosiloxanes V having per molecule at least two alkenyl groups each bonded to the silicon atom, preferably vinyl, and having dynamic viscosities x1 and x2 at 25° C. in the ranges 10 to 1000 mPa·s and from 1000 to 150 000 mPa·s respectively,
  at least 25% by weight, relative to the total weight of said part (A), of at least one stabilizer D selected from the group of starches,
  a catalytically effective amount of at least one catalyst C which is a compound of a metal from a platinum group,
  optionally at least one polyorganosiloxane gum G having per molecule at least two alkenyl, preferably vinyl, groups which are bonded to the silicon, and having a viscosity of greater than 1 000 000 mPa·s at 25° C.,
  optionally at least one reinforcing filler Q1 and/or one bulking filler Q2,
  optionally at least one retarder or inhibitor I of polyaddition reactions,
  optionally at least one polydimethylsiloxane F blocked at each of the chain ends by a trimethylsilyl unit and used as diluent,
  optionally at least one colorant K,
  optionally a paraffin P,
  optionally at least one biocide N,
  optionally at least one wetting agent M,
  optionally at least one silicone resin R, and
(2) part B contains no catalyst C and comprises:
  at least one compound H which is a polyorganosiloxane having per molecule at least three hydrogen atoms bonded to the silicon,
  optionally at least one compound V which is a polyorganosiloxane having per molecule at least two alkenyl, preferably vinyl, groups bonded to the silicon,
  optionally at least one stabilizer D selected from the group of starches,
  optionally at least one polyorganosiloxane gum G having per molecule at least two alkenyl, preferably vinyl, groups which are bonded to the silicon, and having a viscosity of greater than 1 000 000 mPa·s at 25° C.,
  optionally at least one reinforcing filler Q1 and/or one bulking filler Q2,
  optionally at least one retarder or inhibitor I of polyaddition reactions,
  optionally at least one polydimethylsiloxane F blocked at each of the chain ends by a trimethylsilyl unit and used as diluent,
  optionally at least one colorant K,
  optionally a paraffin P,
  optionally at least one biocide N,
  optionally at least one wetting agent M imparting a hydrophilic nature to the surface of said elastomer E or said material M, and
  optionally at least one silicone resin R.

According to one advantageous embodiment, the composition X according to the invention is obtained by mixing parts A and B in weight ratios of between 1:10 to 1:1 respectively, and preferably by mixing, by weight, 1 part of A and 5 parts of B.

Another subject of the invention provides a material M or elastomer E obtained by crosslinking and/or curing the composition X according to the invention and as defined above.

Lastly, a final subject of the invention relates to the use of the composition X according to the invention and as defined above or of the material M or elastomer E according to the invention and as defined above for taking dental impressions, for manufacturing pads employed in pad printing techniques, for producing podiatric orthoses, or for taking an impression of the auditory canal.

This use, in one preferred embodiment, involves ensuring that the crosslinking of the silicone elastomer is initiated by mixing parts A and B, reproducing the impression, and allowing crosslinking to continue until the elastomer has crosslinked sufficiently and is sufficiently hard.

According to another mode of use, the material M or elastomer E as described above is intended for the manufacture of pads such as those used in pad printing techniques, where it is advantageous to have a material that possesses high mechanical properties and has a surface energy that can be modulated by addition of surfactant(s) while retaining the level of fluidity required for the manufacture of pads by molding. This other use, in one preferred embodiment, involves ensuring that the crosslinking of the silicone elastomer is initiated by mixing of parts A and B, forming an object having the shape of the desired pad by molding, in a manner known per se, and allowing crosslinking to continue until the elastomer has crosslinked sufficiently and is sufficiently hard.

Although crosslinking by polyaddition reactions between the polyorganosiloxanes V and H can be initiated and developed even at a temperature in the region of room temperature (23° C.), crosslinking may also be carried out thermally (by heating, for example, at a temperature of from 60° C. to 110° C.) and/or by electromagnetic radiation (accelerated electronic or "electron beam" radiation) and/or by infrared radiation.

The examples below are given to aid comprehension of the present invention, and should not be interpreted as limiting the scope of the present invention.

EXAMPLE a) List of starting materials used:
  Vinyl polyorganosiloxane V-1: polydimethylsiloxane oil blocked at each of the chain ends by a siloxyl unit $(CH_3)_2(Vi)SiO_{1/2}$, with viscosity of 100 000 mPa·s (where Vi=vinyl group).
  Vinyl polyorganosiloxane V-2: polydimethylsiloxane oil blocked at each of the chain ends by a siloxyl unit $(CH_3)_2(Vi)SiO_{1/2}$, with viscosity of 600 mPa·s.
  Polydimethylsiloxane (PDMS) F-1 blocked at each of the chain ends by a siloxyl unit $(CH_3)_3SiO_{1/2}$ and having a viscosity of 50 mPa·s.
  Stabilizer D-1: corn starch.
  Paste 1: Mixture: vinyl polyorganosiloxane V-2 (polydimethylsiloxane oil blocked at each of the chain ends by a siloxyl unit $(CH_3)_2(Vi)SiO_{1/2}$, with viscosity of 600 mPa·s)+a filler Q-1, which is a fumed silica surface-treated with D4 (octamethylcyclotetrasiloxane) in an 85:15 mixture by weight respectively.

Wetting agent M-1: ester obtained by esterifying a $C_{13}$ fatty acid (lauric acid) with a poly(oxyethylene) glycol containing approximately 9 OE units, having an HLB of 13.1, sold under the name Lincol PE 400 ML®.
Catalyst C-1: Platinum.
Bulking filler Q2-1: Sicron SA 600: ground quartz with average particle diameter of 10 mm.
Bulking filler Q2-2: Calcium carbonate Calofort-S.
Bulking filler Q2-3: zeolite (Zeolite 4 A/S).
Colorant K.
Hydrogen polyorganosiloxane H-1: poly(dimethyl)(hydrogenomethyl)siloxane blocked at each of the chain ends by a siloxyl unit $H(CH_3)_2SiO_{1/2}$, having a viscosity of 300 mPa·s.

Mixing can be carried out either by hand in a beaker or by means of a laboratory metering machine. Evaluation takes place after 7 days and 25 days at 60° C. of the following:
the working time (W.T. in minutes and seconds) of the compositions resulting from the mixtures of parts A and B as set out above and in accordance with standard ISO 4823;
the elastic memory in accordance with standard ISO 4823; and
the Shore A hardness (SAH) after 8 minutes of crosslinking.

After 25 days at 60° C., the presence or absence of blackening of the cartridge containing the catalyst (part A) is ascertained.

The results are set out in table 3.

TABLE 1

Formulations of parts A of the two-component systems

| Components (p/w) | Comparative 1 | Comparative 2 | Comparative 3 | Comparative 4 | Comparative 5 | Example 1 | Example 2 | Example 3 |
|---|---|---|---|---|---|---|---|---|
| Vinyl polyorganosiloxane V-1 | 19.0 | 19.0 | 19.0 | 19.0 | 19.0 | 13.8 | 19.0 | 19.0 |
| Vinyl polyorganosiloxane V-2 | 16.0 | 16.0 | 16.0 | 16.0 | 16.0 | 7.0 | 16 | 16 |
| PDMS F-1 | 15.5 | 15.5 | 15.5 | 15.5 | 15.5 | 15.0 | 15.5 | 15.5 |
| Stabilizer D-1 | 22.5 | 22.5 | 22.5 | 0 | 22.5 | 34.0 | 49.5 | 49.5 |
| Bulking filler Q2-2 | 27.0 | 27.0 | 22.0 | 0 | 27.0 | 0 | 0 | 0 |
| Bulking filler Q2-1 | 0 | 0 | 0 | 39.5 | 0 | 5.0 | 0 | 0 |
| Bulking filler Q2-3 | 0 | 0 | 5.0 | 10.0 | 0 | 0.0 | 0 | 0 |
| Paste 1 | 0 | 0 | 0 | 0 | 0 | 25.0 | 0 | 0 |
| Wetting agent M-1 | 0 | 0 | 0 | 0 | 0 | 0.2 | 0 | 0 |
| Catalyst C-1 (ppm) | 240 | 375 | 240 | 240 | 253 | 100 | 240 | 240 | p/w = parts by weight

TABLE 2

Single formulation for all of the parts B of the two-component systems

| Components (p/w) | Amount parts by weight |
|---|---|
| Vinyl polyorganosiloxane V-1 | 22.75 |
| Vinyl polyorganosiloxane V-2 | 4.80 |
| Stabilizer D-1 | 37.80 |
| Paste 1 | 20.00 |
| Wetting agent M-1 | 0.15 |
| Polyorganosiloxane H-1 | 4.00 |
| Bulking filler Q2-1 | 9.99 |
| Colorant K | 0.40 |

TABLE 3

Properties measured for each material obtained from the two component systems

| Properties | Comparative 1 | Comparative 2 | Comparative 3 | Comparative 4 | Comparative 5 | Example 1 | Example 2 | Example 3 |
|---|---|---|---|---|---|---|---|---|
| W.T. | 2'00" | 1'45" | 1'55" | 2'10" | 2'05" | 1'45" | 1'42" | 1'50" |
| SAH at t = 0 | 17.5 | 25.2 | 20 | 17.0 | 20.5 | 20.5 | 21 | 20 |
| W.T. | 1'55" | Not measured | 1'55" | 2'50" | 2'50" | Not measured | 2'00" | 2'05" |
| SAH after 7 days at 60° C. | 15.6 | | 19.0 | 18.5 | 13.5 | | 18 | 17 |
| W.T./ SAH after 25 days at 60° C. | Total inhibition; no elastomeric material is obtained | | | | | 2'10" / 15 | 2'15" / 15 | 2'30" / 11 |
| Blackening of the cartridge containing the catalyst (part A) after 25 days at 60° C. | YES | YES | YES | YES | YES | NO | NO | NO |

For each two-component system under test, parts A and B, packaged in the form of cartridges, are placed in an oven and undergo accelerating aging at 60° C. After durations of 7 days and 25 days, the properties of the resultant materials are evaluated by crosslinking, at an ambient temperature at 23° C., a composition obtained by mixing 5 parts by weight of part B with one part by weight of a part A.

Comparatives tests 1, 2, 3 and 5 show that even when the stabilizer D is present in part A, and at relatively high levels (22.5% by weight, relative to the total weight of part A), this does not prevent blackening of the cartridge containing the catalyst (part A) after 25 days of storage at 60° C. This is no longer the case for examples 1, 2, and 3 according to the invention, which no longer exhibit this problem of black ening of the parts A comprising the platinum catalyst. Moreover, after aging for 25 days at 60° C. of parts A and B before use, it is observed that the examples according to the invention produce an elastomer having a working time which is acceptable for use in the field of the taking of dental impressions.

The invention claimed is:
1. A storable composition comprising:
(a) 30% to 49.5% by weight, relative to the total weight of the composition, of at least one stabilizer D selected from the group of starches;
(b) at least one polyorganosiloxane V-1 having a viscosity of between 1000 mPa·s and 200,000 mPa·s and having per molecule at least two alkenyl groups, which are each bonded to a silicon atom;
(c) at least one polyorganosiloxane V-2 having a viscosity of between 10 mPa·s and 1000 mPa·s and having per molecule at least two alkenyl groups, which are each bonded to a silicon atom; and
(d) at least one catalyst C which is a compound of a metal from the platinum group;
wherein the composition has a weight ratio of polyorganosiloxane V-1 to polyorganosiloxane V-2 of from about 2:1 to about 1.2:1; and
wherein the composition exhibits no blackening after 25 days at 60° C. and is storable for at least one year.

2. The composition as defined by claim 1, wherein the at least one stabilizer D is a corn starch, an acid-treated starch, a base-treated starch, a bleached starch, an oxidized starch, an enzyme-treated starch, a monostarch phosphate, a glycerol starch, a distarch phosphate esterified with sodium trimetaphosphate, a phosphated distarch phosphate, an acetylated distarch phosphate, a starch acetate esterified with acetic anhydride, a starch acetate esterified with vinyl acetate, an acetylated distarch adipate, an acetylated distarch glycerol, a hydroxypropyl starch, a hydroxylated distarch phosphate, a hydroxypropyl distarch glycerol, or a sodium starch octenyl succinate.

3. The composition as defined by claim 1, further comprising at least one compound selected from the group consisting of:
a reinforcing filler Q1,
a bulking filler Q2,
a retarder or inhibitor I of polyaddition reactions,
a polyorganosiloxane gum G having per molecule at least two alkenyl, groups which are bonded to the silicon, and having a viscosity of greater than 1000 mPa·s at 25° C.,
a diluent comprising a polydimethylsiloxane F,
a colorant K,
a plasticizer P selected from the group consisting of liquid petroleum jelly and a paraffin,
a wetting agent M,
a silicone resin R,
and a biocide N.

4. The composition as defined by claim 1, wherein the at least one stabilizer D is a corn starch.

5. The composition as defined by claim 3, wherein the wetting agent M is a surfactant.

6. The composition as defined by claim 3, wherein the polydimethylsiloxane F has a dynamic viscosity of between 10 mPa·s and 5000 mPa·s.

7. A mixture comprising the composition as defined by claim 1, wherein the composition of claim 1 is a part A and is mixed with a part B in a weight ratio of between 1:10 to 1:1, respectively, to obtain the mixture;
wherein the part B of the mixture comprises:
(e) at least one polyorganosiloxane H having per molecule at least two hydrogen atoms which are bonded to an identical or different silicon atom;
(f) at least one compound V comprising a polyorganosiloxane having per molecule at least two alkenyl groups bonded to a silicon, wherein the number of hydrogen atoms bonded to the silicon in the polyorganosiloxane H to the total number of alkenyl unsaturation in the compound V is a ratio between 0.4 to 10; and
wherein part A and part B are crosslinkable and/or curable by polyaddition reaction.

8. The composition as defined by claim 1, wherein the polyorganosiloxane V-1 further comprises:
(a) at least two siloxyl units of formula:

$$T_a Z_b SiO_{\frac{4-(a+b)}{2}} \quad (1.1)$$

in which:
the symbols T are identical or different $C_2$-$C_6$ alkenyl groups,
the symbols Z are identical or different monovalent hydrocarbon groups selected from the group consisting of an alkyl having 1 to 8 carbon atoms inclusive, optionally substituted by at least one halogen atom, and an aryl, and
a is 1 or 2, b is 0, 1, or 2, and the sum a+b is 1, 2, or 3; and
(b) optionally at least one siloxyl unit of formula:

$$Z_c SiO_{\frac{4-c}{2}} \quad (1.2)$$

wherein:
the symbol Z has the same meaning as above and c is 0, 1, 2, or 3.

9. The mixture as defined by claim 7, wherein:
(1) part A further comprises at least one additive selected from:
at least one polyorganosiloxane gum G having per molecule at least two alkenyl, groups which are bonded to the silicon, and having a viscosity of greater than 1,000,000 mPa·s at 25° C.,
at least one reinforcing filler Q1 and/or one bulking filler Q2,
at least one retarder or inhibitor I of polyaddition reactions,
a diluent comprising at least one polydimethylsiloxane F blocked at each of the chain ends by a trimethylsilyl unit,
at least one colorant K,
a paraffin P,
at least one biocide N,
at least one wetting agent M, and
at least one silicone resin R; and
(2) part B does not comprise a catalyst C and further comprises at least one additive selected from:
at least one stabilizer D selected from the group of starches,
at least one polyorganosiloxane gum G having per molecule at least two alkenyl groups which are bonded to the silicon, and having a viscosity of greater than 1,000,000 mPa·s at 25° C., at least one reinforcing filler Q1 and/or one bulking filler Q2, at least one retarder or inhibitor I of polyaddition reactions, a diluent comprising at least one polydimethylsiloxane F blocked at each of the chain ends by a trimethylsilyl unit, at least one colorant K, a paraffin P, at least one biocide N, at least one wetting agent M imparting a hydrophilic nature to the surface of said elastomer E or said material M, and at least one silicone resin R.

10. A material M or elastomer E obtained by crosslinking and/or curing the mixture as defined by claim 7.

11. A method of making dental impressions, pads employed in pad printing techniques, podiatric orthoses, or an impression of an auditory canal, the method comprising making the dental impressions, pads, orthoses or impression using the composition as defined by claim 1.

12. The composition as defined by claim 1, wherein the at least two alkenyl groups are vinyl groups.

13. The composition as defined by claim 3, wherein the at least two alkenyl groups are vinyl groups.

14. The composition as defined by claim 6, wherein the polydimethylsiloxane F has a dynamic viscosity between 20 mPa·s and 1000 mPa·s.

15. The mixture as defined by claim 7, wherein part A and part B are mixed by weight, in a ratio of 1 part of the composition and 5 parts of B.

16. The composition as defined by claim 9, wherein one or more alkenyl groups present in the composition are vinyl groups.

17. The composition as defined by claim 8, wherein the amount by weight of the catalyst C, calculated by weight of platinum metal, is from 100 ppm to 240 ppm based on the sum of the total weight of the polyorganosiloxane V-1 and polyorganosiloxane V-2.

18. The mixture as defined by claim 7, wherein the at least one compound V comprises a polyorganosiloxane V-1 and a polyorganosiloxane V-2.

19. A storable composition comprising:
(a) 30% to 49.5% by weight, relative to the total weight of the composition, of at least one stabilizer D selected from the group of starches;
(b) at least one polyorganosiloxane V-1 having a viscosity of between 1000 mPa·s and 200,000 mPa·s and having per molecule at least two alkenyl groups, which are each bonded to a silicon atom;
(c) at least one polyorganosiloxane V-2 having a viscosity of between 10 mPa·s and 1000 mPa·s and having per molecule at least two alkenyl groups, which are each bonded to a silicon atom; and
(d) at least one catalyst C which is a compound of a metal from the platinum group;
wherein the composition has a weight ratio of polyorganosiloxane V-1 to polyorganosiloxane V-2 of from 1.97:1 to 1.1875:1; and
wherein the composition exhibits no blackening after 25 days at 60° C. and is storable for at least one year.

* * * * *